United States Patent
Sorensen et al.

(10) Patent No.: US 8,554,953 B1
(45) Date of Patent: *Oct. 8, 2013

(54) ADVANCED LOGIC SYSTEM DIAGNOSTICS AND MONITORING

(75) Inventors: Steen Ditlev Sorensen, Scottsdale, AZ (US); Sten Sogaard, Anthem, AZ (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/914,737

(22) Filed: Oct. 28, 2010

Related U.S. Application Data

(62) Division of application No. 12/026,703, filed on Feb. 6, 2008, now Pat. No. 7,870,299.

(51) Int. Cl.
*G06F 3/00* (2006.01)

(52) U.S. Cl.
USPC .................. 710/2; 714/30; 714/47.1; 714/49

(58) Field of Classification Search
USPC ............................................................ 710/2
See application file for complete search history.

(56) References Cited

U.S. PATENT DOCUMENTS

| | | | |
|---|---|---|---|
| 3,942,158 A | 3/1976 | Dummermuth | |
| 4,249,248 A | 2/1981 | Yomogida et al. | |
| 4,326,263 A | 4/1982 | Given | |
| 4,442,504 A | 4/1984 | Dummermuth et al. | |
| 4,535,456 A | 8/1985 | Bauer et al. | |
| 4,804,515 A | 2/1989 | Crew et al. | |
| 4,839,852 A | 6/1989 | Knutsen | |
| 5,056,001 A | 10/1991 | Sexton | |
| 5,978,593 A | 11/1999 | Sexton | |
| 6,138,250 A * | 10/2000 | Nouri et al. | 714/31 |
| 6,167,547 A | 12/2000 | Senechal et al. | |
| 6,243,838 B1 * | 6/2001 | Liu et al. | 714/57 |
| 6,526,461 B1 * | 2/2003 | Cliff | 710/100 |
| 6,701,258 B2 | 3/2004 | Kramb et al. | |
| 6,956,920 B1 * | 10/2005 | Veenstra et al. | 375/372 |
| 7,320,103 B2 * | 1/2008 | Filipovic | 714/799 |
| 2003/0033374 A1 * | 2/2003 | Horn et al. | 709/217 |
| 2003/0135802 A1 * | 7/2003 | Klein et al. | 714/725 |
| 2004/0003313 A1 * | 1/2004 | Ramirez | 714/6 |
| 2004/0083308 A1 * | 4/2004 | Sebastian et al. | 709/248 |
| 2005/0198404 A1 * | 9/2005 | Kawakami et al. | 710/1 |
| 2008/0133789 A1 * | 6/2008 | McNutt et al. | 710/30 |

* cited by examiner

*Primary Examiner* — Elias Mamo
(74) *Attorney, Agent, or Firm* — Mark V. Loen

(57) ABSTRACT

The Advanced Logic System (ALS) is a complete control system architecture, based on a hardware platform rather than a software-based microprocessor system. It is significantly different from other PLC-type control system architectures, by implementing a FPGA in the central control unit. Standard FPGA logic circuits are used rather than a software-based microprocessor which eliminate problems with software based microprocessor systems, such as software common-mode failures. It provides a highly reliable system suitable for safety critical control systems, including nuclear plant protection systems. The system samples process inputs, provides for digital bus communications, applies a control logic function, and provides for controlled outputs. The architecture incorporates advanced features such as diagnostics, testability, and redundancy on multiple levels. It additionally provides significant improvements in failure detection, isolation, and mitigation for the highest level of integrity and reliability.

4 Claims, 8 Drawing Sheets

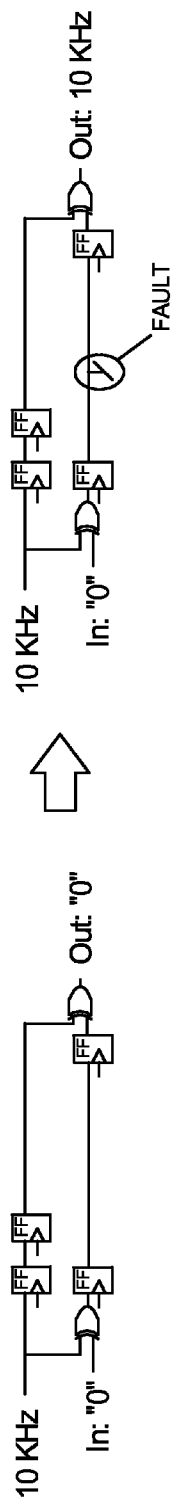

ADVANCED LOGIC SYSTEM DIAGNOSTICS AND MONITORING

CROSS REFERENCE TO RELATED APPLICATIONS

This is a divisional application of U.S. application Ser. No. 12/026,703 filed on Feb. 6, 2008. The prior referenced application is hereby incorporated by reference.

STATEMENT REGARDING FEDERALLY SPONSORED RESEARCH OR DEVELOPMENT

Not applicable.

REFERENCE TO SEQUENCE LISTING, A TABLE, OR COMPUTER PROGRAM LISTING

Not applicable.

BACKGROUND OF THE INVENTION (1) Field of the Invention

The present invention is applicable to industrial process monitoring and control. The present invention is particularly directed toward safety critical control systems, including nuclear plant reactor protection systems, where reliability and integrity are of the highest importance.

(2) Description of Related Art

In the field of industrial control systems, including process control systems, redundant monitoring and control paths are used to ensure reliable operation. In the nuclear power industry, it is common to use several levels of redundancy to assure that a particular measurement is known to be valid. In nuclear power plants, independent shut-down and safe-operation systems are added to monitor operational and safety related parameters throughout the control processes. In the event a measurement indicates an unsafe condition, the system enters a safe operational mode, or alternately, operated safely according to predetermined logic. It is critical that the safety related control system, known as a plant protection system, operates with an exceptionally high level of reliability and predictability.

One difficulty in creating a reliable plant protection system is the use of a software based microprocessor. Software has inherent operational problems that are difficult to resolve. Even relatively simple systems require a significant amount of program code. A software-microprocessor system is subject to common mode failure where redundant systems may fail simultaneously due to a fault condition.

In spite of redundancy that may be included within software-microprocessor systems, a fault may occasionally affect enough redundant functions that it is not possible to correctly pick a non-faulty result, and the system will experience a common-mode failure. The common-mode failure may result from a single fault or several faults. It is known that microprocessor based systems are vulnerable to common-mode failures where redundant copies of software fail under the same fault.

The common-mode fault, in particular, makes software-microprocessor systems undesirable in a plant protection system.

Others have worked on various aspects of plant protection systems. For example, U.S. Pat. No. 6,701,258 describes a system for a plant protection system utilizing distributed voting logic. The system does not include sufficient redundancy in communications or control logic to be suitable for a safety critical system.

U.S. Pat. No. 6,167,547 describes a fault logic scheme for a plant protection system. Although a logic decision structure is described, it is only a small part of an actual plant protection system. Other important and vital features needed for redundant and reliable system monitoring are not described.

U.S. Pat. No. 4,804,515 describes a redundant path system suitable for a very complicated control system. Independent channels measure and communicate the same process information and are monitored by software based microcomputers. The parallel configuration and redundancy requires many software based microcomputers. The complexity of the system increases the number of components, and therefore, reducing the reliability of the system.

Others have worked on controller systems. The following US patents describe microprocessor based programmable controller systems which utilize software programming: U.S. Pat. No. 5,978,593, U.S. Pat. No. 5,056,001, U.S. Pat. No. 4,839,852, U.S. Pat. No. 4,442,504, U.S. Pat. No. 4,326,263, U.S. Pat. No. 4,249,248, and U.S. Pat. No. 3,942,158. They all have problems associated with software based systems previously described, and they have not been architecturally designed with the kind of redundancy suitable for a safety critical system or a system demanding high reliability.

U.S. Pat. No. 4,535,456 describes a method of monitoring one microprocessor by utilizing another microprocessor. It is not a parallel operation by utilizing redundant or duplicated control logic and is therefore undesirable for a safety critical system or a system demanding high reliability.

BRIEF SUMMARY OF THE INVENTION

The advanced logic system (ALS) is a complete control system architecture, based on a hardware platform rather than a software-based microprocessor system. It is significantly different from other software based microprocessor control system architectures, such as a Programmable Logic Controller (PLC) type, by implementing a Field Programmable Gate Array (FPGA) with a simple logic circuit in the central control unit, as opposed to a microprocessor complex with all the required peripherals. The FPGA logic circuits are used to eliminate problems with software based microprocessor systems, such as software common-mode failures. It provides a highly reliable system suitable for safety critical control systems, including reactor protection systems in nuclear plants. The system samples process inputs, provides for digital bus communications, applies a control logic function, and provides for controlled outputs. The architecture incorporates advanced features such as diagnostics, testability, and redundancy on multiple levels. It additionally provides significant improvements in failure detection, isolation, and mitigation to achieve the highest level of integrity and reliability. The ALS offers significant improvements in operability and maintainability compared to other architectures, as well as full flexibility and modularity.

BRIEF DESCRIPTION OF THE SEVERAL VIEWS OF THE DRAWING(S)

FIGS. 7A-7D illustrates the strategy used by the present invention to avoid any un-detectable faults.

DETAILED DESCRIPTION OF THE INVENTION

Figure 1:
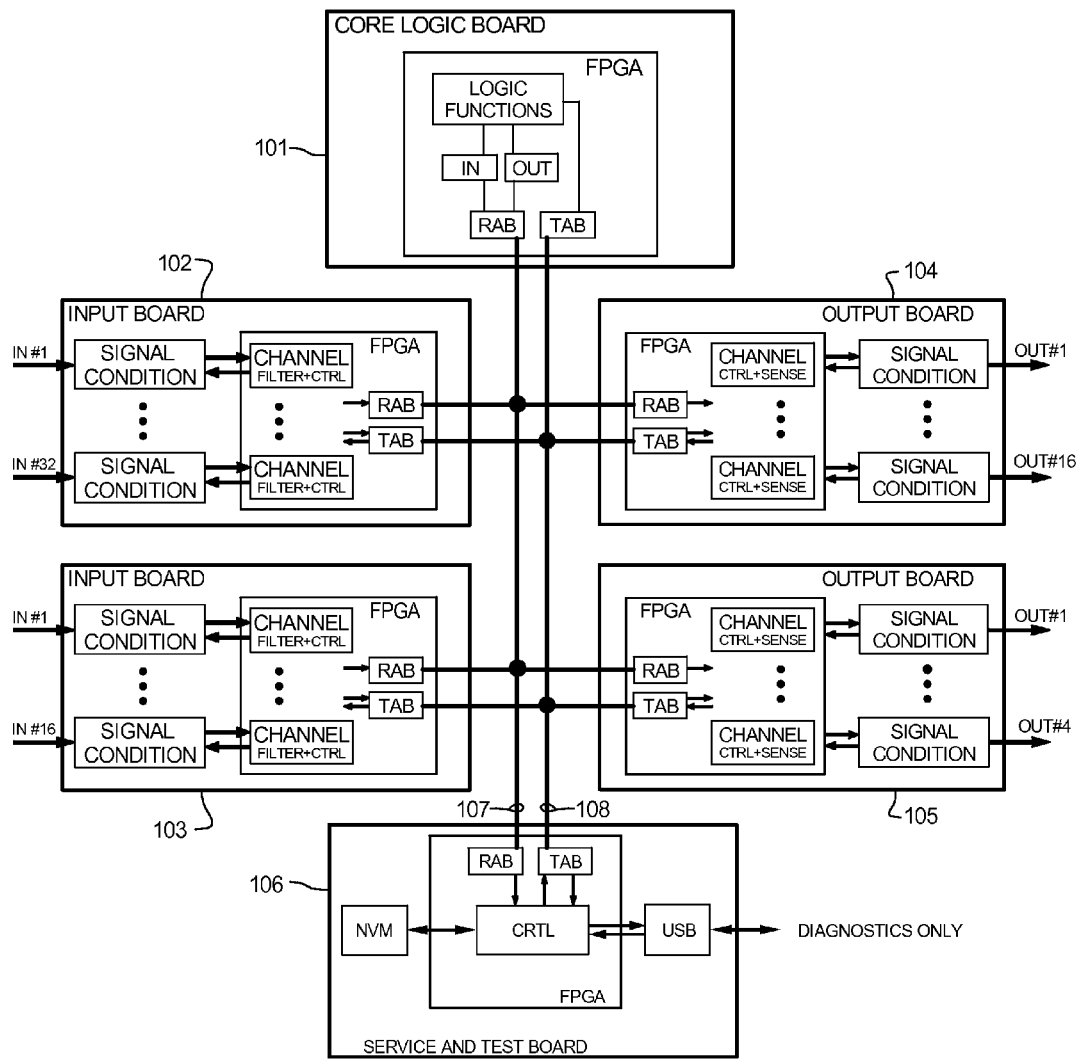
FIG. 1 is a general schematic of the main features of the present invention.

A description of terms related to the present invention follows.

Advanced Logic System (ALS) is a general title of the hardware architecture platform for the present invention. The ALS is a digital logic controller that is used to monitor and control a process.

A Field Programmable Gate Array (FPGA) is a semiconductor device containing programmable logic components referred to as "logic blocks," or "programmable interconnects." FPGAs are known in the art.

A circuit board refers to a printed circuit board (PCB), also known as board, a card, or a module.

A channel is the term used for a circuit, which independently can measure or detect a field input, or control a field output. A board typically has a number of channels, such as 4, 8, 16, or 32 channels per board, but other numbers are possible. A channel will typically include signal conditioning, a self test feature, various basic control features, and surge suppression.

A rack contains a number of boards. The front of a rack is referred to as the front-panel, and may be implemented with a number of customizable and application specific front-plates (also referred to as face-plates). One common rack size is 6 KU/19" chassis.

Rack inputs and outputs are referred to as signals. Typically an input or output signal comprise of a 2-wire connection with the signal and its return. The term input and output are always referenced from the ALS rack perspective.

An Assembly Panel typically contains a number of terminal blocks, fuse blocks, relays, electro magnetic filters, surge suppressors, as well as all associated wiring.

A cabinet may house multiple racks as well as a number of assembly panels.

The rear, externally facing side of a rack is referred to as the rear-panel.

An I/O circuit board is a circuit board that is capable of receiving at least one item from the group of: input signal, output signal, digital communication, and external digital communication to an external device. I/O circuit boards often include both input and output signals, as well as digital communication to the core logic controller. The term I/O circuit board would include input boards, output boards, and communication boards such as a service and test board.

In a preferred embodiment of the present invention, front-plates are attached to the boards, and when all boards are inserted into the back-plane they will comprise a complete front-panel. Latching injection/ejection handles may be mounted on the front-plates to provide a locking mechanism to secure the boards in the rack. All wiring to and from the rack is normally done through the rear-panel using rear-panel connectors.

In a preferred embodiment, an application specific back-plane is attached to the internally facing side of the rear-panel. The back-plane connects the rear-panel connectors (facing away from the rack) to the board connectors (facing into the rack).

Field inputs and outputs are used to identify the signals entering or exiting the cabinet and are typically connected to a terminal-block located in the cabinet. Field inputs and outputs are typically connected directly to the ALS rack, but may be connected to components located on the assembly panel.

Typical field inputs from a process are known in the art and include, but are not limited to, valve positions, process flows, pressures, temperatures, alarms, activated circuits, control sequencing, speeds, current, voltage, power, switch positions, position indicators, various sensors, etc. The amount and type of information depends upon the process being monitored.

Typical field outputs that provide a control function for a process are known in the art and include, but are not limited to, activating valves, activating switches, alarm annunciation, displaying operator warning notices, displaying operator information, operating control loops, activating electrical relays, activating motors, operating process equipment, etc. The amount and type of process control depends upon the process being controlled or protected.

As a preferred embodiment, circuit boards may have a front-plate attached on the front-edge and male connectors on the back-edge to connect the board to the back-plane. Each circuit board connected to a communication bus normally has at least one FPGA and several support components. The support components may include any of resistors, capacitors, inductors, analog and digital ICs such as voltage regulators/voltage supervisors/74xxx drivers/etc, as well as the necessary connectors and Light Emitting Diodes (LEDs).

In a preferred embodiment, any circuit board may be inserted and removed from a rack without the need for a human to touch any wiring, such as when wires have to be disconnected, reconnected, or manually moved out of the way by a hand or hand tool. In a preferred embodiment, the circuit boards may be inserted into the back-plane with force only applied to the front plate.

The ALS platform incorporates advanced features to allow for diagnostics, testability, and modularity. It is designed to be at the appropriate level of complexity to achieve high reliability and integrity as well as allow enough flexibility to target multiple safety critical applications within a given plant. Diagnostics and testing capabilities are designed into the ALS platform to ensure there is a systematic approach to maintaining and testing the system.

The ALS platform is scalable and flexible, allowing for the appropriate level of complexity and maintaining high reliability and integrity. It allows the ready expansion to control of a large process utilizing the same design architecture for a large number of field inputs and outputs to monitor and control.

The preferred embodiment of the present invention is to utilize FPGAs to implement the primary control functions. In other embodiments, alternatives to FPGAs are used which include ASICs (Application Specific Integrated Circuits), CPLD (Complex Programmable Logic Device), Gate Arrays, and PAL (Programmable Array Logic). These devices are generally called programmable logic devices or complex logic devices. ASICs are typically used for complex devices such as processors, graphics controllers, or for very high volume consumer products. All of these devices may be utilized through suitable programming to operate without the use of executable software. A system governed by these devices could be described as hardware based.

FPGAs are popular in end products such as space and aerospace products. FPGAs are subject to rigorous quality assurance processes and procedures, and long product cycles are common.

Fault-tolerance or graceful degradation is an important feature of the present invention. Preferably, the FPGA is programmed to allow the system being controlled to continue operation in the event of the failure of certain portions of the input/output boards, inconsistencies between input variables, temporary problems in communication, non-critical hardware component failures, or non-critical communication failures. In addition, redundant monitoring of a process input may allow normal operation by a use of a voting scheme. However, these various non-critical failures potentially decrease the ability of the overall system to function normally, even if the fault is non-critical. The FPGA is preferably programmed so that suitable action, defined during a system configuration, is taken whenever there is a failure. If an action is required, the action normally is reflected by a directive change to the output boards. The suitable action would include directing an output board to enter a fail safe mode.

An FPGA is programmed utilizing logic which is customizable based on the requirements of a given application, and may contain any type of digital building blocks which can be generated from a NAND2 device, which includes, but is not limited to, AND/OR/XOR gates, Flip Flops (D, JK, SR), counters, timers, multiplexers, or Finite State Machines (FSMs). When programmed properly, the FPGA will behave in a highly predictable, substantially deterministic manner by utilizing these programming blocks.

FIG. 1 shows a preferred embodiment of the present invention. The ALS platform is based on four basic types of boards, and is configured to suit a specific application. The Core Logic Board (CLB) 101 is responsible for all control related activities and primary communication in the system. A number of Input Boards (IPBs) 102, 103 are responsible for conditioning, sensing, filtering, and sampling field input signals from field inputs. A number of Output Boards (OPBs) 104, 105 are responsible for controlling and conditioning field output devices on field outputs. The Service and Test Board (STB) 106 is responsible for independent monitoring of system integrity, diagnostics, and communication. Preferably, in addition to these four types of boards, the ALS system also contains redundant Power Supply Boards (PSB) which are not shown.

In a preferred embodiment, board to board communication is supported using two independent digital serial data busses: a Reliable ALS Bus (RAB) 107 and a Test ALS Bus (TAB) 108. These two busses then comprise the ALS bus communication network. Another embodiment is to utilize a third independent bus that performs the same function of the RAB in parallel for redundancy and independence. Any number of busses may be used, including only one bus. The RAB is used for all data transfers between ALS boards during normal system operation, and the TAB is used for integrity monitoring, diagnostics information, and test information. The RAB is utilized for primary monitoring and control by transferring safety related signal information between boards. The Core Logic Board is master on the RAB and the Service and Test Board is master on the TAB. The digital communication bus architecture is preferably a simple differential EIA-485 or EIA-422, point-to-point, master-slave communication protocol with suitable communication protocols and standard Cyclic Redundancy Checks (CRC) protection to ensure the integrity of the communicated information between two boards.

The EIA-485 (formerly RS-485) standard is an OSI Model physical layer electrical specification of a two wire, half-duplex, multipoint serial connection. The standard specifies a differential form of signaling. The difference between the wires' voltages is what conveys the data. One polarity of voltage indicates logic 1 level; the reverse polarity indicates logic 0. The difference of potential must be at least 0.2 volts for valid operation. EIA-485 only specifies electrical characteristics of the driver and the receiver, and does not specify the communication protocol.

The EIA-422 standard specifies the "Electrical Characteristics of Balanced Voltage Digital Interface Circuits" and is known in the art. The standard provides for data transmission by use of balanced or differential signaling.

FIG. 1 illustrates the use of a number of input and output boards. This is an illustration of how the ALS architecture may be scaleable and configured for a particular application.

In a preferred embodiment, each input board and output board includes an onboard FPGA. This provides for self checking capabilities, and the onboard FPGA may include programming logic that will allow various status indicators to be communicated on the RAB and TAB by the value of one or more bits in the communication. In a preferred embodiment, the onboard FPGA includes bus communication logic, integrity monitoring logic, a built in self test logic, and optionally, a control logic circuit.

The RAB and TAB buses are designed to prevent 'data storm' problems by the use of a fixed hardware scheduler. Bus communication is data independent and the communication protocol schedule is therefore not modifiable. This prevents data overload or tampering in the system.

Both RAB and TAB busses are implemented without data dependency. That is, when communication is dependent upon the data values within the data transmissions. Data dependencies are known to lead to common mode failures as well as unpredictable circuits. The use of a FPGA with logical circuits where the bus communication network is implemented as a pipe, which just streams data with no knowledge of the content prevents this type of a situation.

Preferably, the RAB and TAB communicate to a serial link transceiver on each board which is connected to a defined communication module within an onboard FPGA. Additionally, suitable electronic driver hardware and a backbone are also included. Preferably, the communication link incorporates a serial driver with an enable pin controlled by a redundancy check circuit.

In a preferred embodiment the bus communication network operates independently of any signal conditioning, signal filtering, and signal control on any circuit board. Processing is more reliable if any bus will continue to operate regardless of how a circuit board processes data internally. Also, any bus communication is preferably not interruptible by external communication to perform diagnostic checks or external requests for information.

Preferably, the physical layer of the RAB and TAB are each based on bit serial communication. Additionally the physical layer of the bus communication network is based on a point to point bus communication topology. That is, the bus communication network communicates from one FPGA on a circuit board to another FPGA on a separate circuit board.

To improve reliability, in a preferred embodiment, all digital communication circuits are implemented using redundant cores within onboard FPGA's to enable detection and mitigation of any failure within the bus communication network. An independent circuit detects any discrepancy between redundant logic cores within the complex logic devices by use of gating and XOR checks. Any discrepancy will result in a disablement of communication and a resulting fail safe state.

Figure 2:
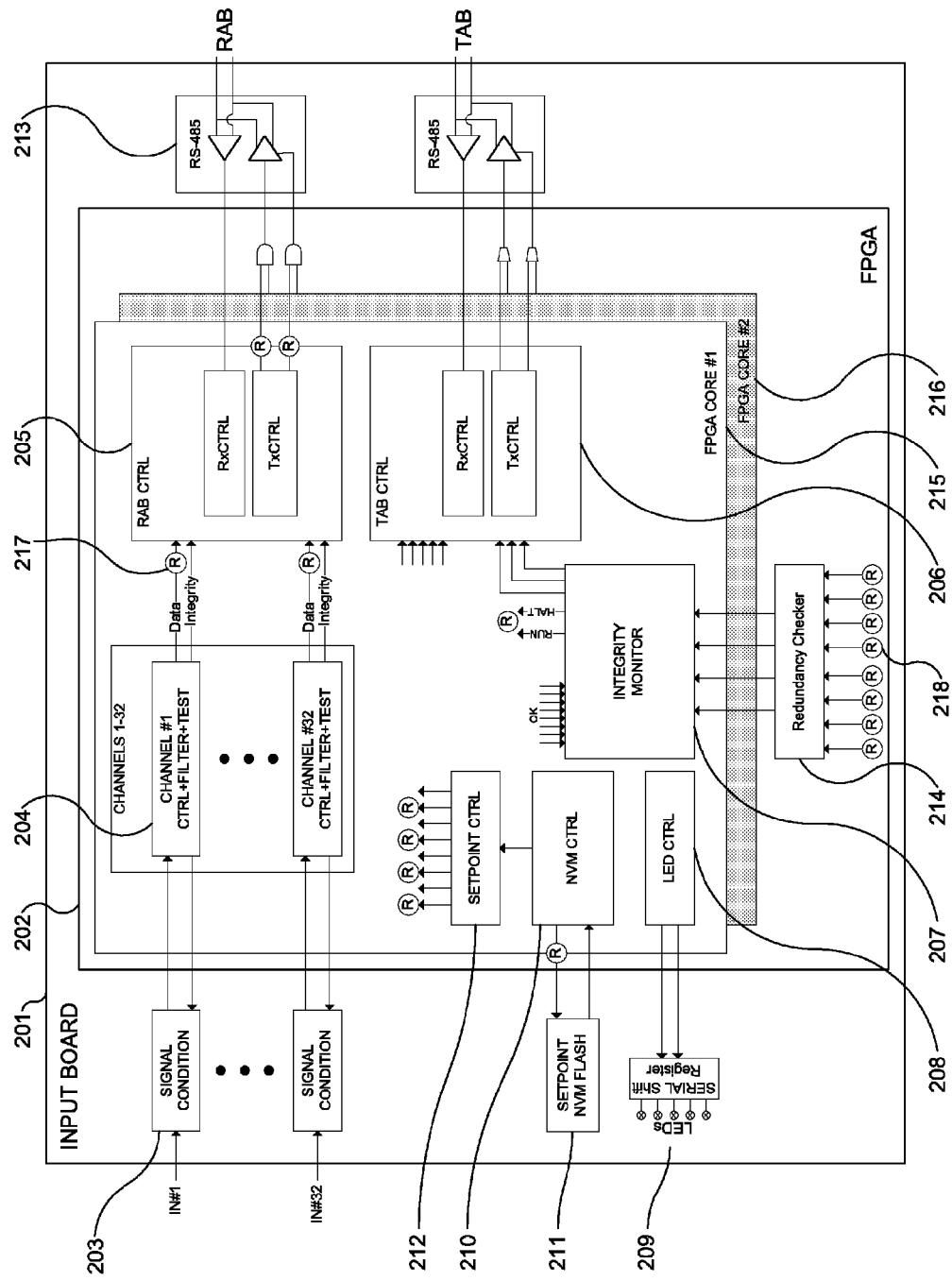
FIG. 2 is a general arrangement of an input control board.

FIG. 2 is a preferred embodiment of a generic input board 201 (IPB). IPBs are responsible for conditioning, sensing, filtering, and sampling field inputs signals. Boards are typically dedicated to a specific input type, such as 24V or 48V or 125V digital inputs, 4-20 mA or 0-10V analog inputs, RTD or thermo-couple inputs. The inputs can be from an electrical contact, a resistance temperature detector, a thermocouple device, sensors with a current output source typically up to 60 milliamps, voltage input with a typical maximum of 5 to 260 volts, resistive input, and variety of communication type inputs.

The IPB preferably provides a front panel indication which shows the status of a particular input using an LED 209. An LED controller 208 creates the outputs needed for LED indicators 209 which may include any number of LEDs. The LEDs are preferably used to indicate that the board is in the ready mode, power is on, failure mode, state of the channel, and operating normally.

Preferably the IPB has self testing circuits within the onboard FPGA 202 to detect a power failure, input channel failures, and circuit failures within the FPGA itself. The self test circuit then causes an LED indication of failure on the front panel of the IPB. The onboard FPGA failure is detectable by an internal redundancy checker 214 so that any failure is instantly detected.

An ALS rack may require multiple IPBs to support a particular application. The number of IPBs in the ALS rack is related to the number of channels and the type of field inputs required. The input channel to a particular IPB can be simple with minimal circuitry to measure a digital signal, or it can contain more complex feedback measuring and test circuitry to ensure channel integrity.

An input channel comprises of two key circuits: the analog signal conditioning circuit 203 and a digital channel circuit 204. The analog signal conditioning circuit 203 is responsible for converting field input signals into digital representation, as well as protection of the circuits from field transients. The digital channel circuits 204 is located in the FPGA 202 and performs all channel control, sample and hold, digital filtering functions, integrity checks, and self-testing. The digital channel circuits, RAB communication, and channel integrity are implemented with redundant logic within the FPGA.

Preferably, the input channels are divided into groups. Preferably, each group uses a common ground and has galvanic isolation from the other groups as well as isolation from the digital circuits of the board.

Incorporated into the FPGA 202 is the digital channel circuit 204, the Setpoint controller 212, NVM controller 210, LED controller 208, Integrity monitor 207, RAB communication controller 205, TAB communication controller 206, and the Redundancy Checker 214.

The input board has an application specific setpoint configuration that is stored locally. The setpoint information is retrieved at power up from a dedicated FLASH device 211 using a non volatile memory (NVM) controller 210. The setpoint configuration is stored in an external Non-Volatile Memory (NVM) FLASH device 211 and local copies are maintained and utilized in the setpoint controller 212 within redundant cores in the FPGA. The amount of setpoint information stored is commonly between 0-80 bytes. Typical setup information is enable/disable, filter time constants, normal open/close contacts, and build information such as board ID and build dates.

In a preferred embodiment, the control, filtering, testing, TAB communications, and RAB communications, are all performed within two redundant logic cores 215, 216 in the FPGA 202. At key redundancy check points (a typical point is shown 217 which is additionally indicated by the letter R), the signals from a particular circuit from each of the redundant logic cores 215, 216 are wired 218 to a redundancy checker circuit 214. The redundancy checker 214 then compares the two signals from each of the redundant cores for an exact match. If the values do not match, an IPB redundancy failure is detected. This will force the IPB into a fail safe state, and all communication from the IPB to the RAB will be discontinued. Subsequently, the operator will have the capability to see the type of failure through the TAB communication interface 206. Any number of signals from critical circuits may be chosen for redundancy checking in this manner.

The IPB communicates over the RAB 205 and the TAB 206 as requested. In a preferred embodiment, the IPB is a slave device on both the RAB and the TAB, and the communication is via RS-485 (i.e. EIA-485) standard 213. The IPBs are dedicated to providing a new measurement on the RAB every time a request is made. In the event of a detection of a communication failure on the RAB, then the IPB is responsible for isolating the board from further communication on the RAB until the failure(s) has been removed. The communication failure is preferably detected with CRC checking of the communicated packets on the RAB, or by the integrity monitor 207 which also contains a hardware watchdog feature. The watchdog feature times-out after unsuccessful communication after a set period of time, typically greater than 100 ms.

Figure 3:
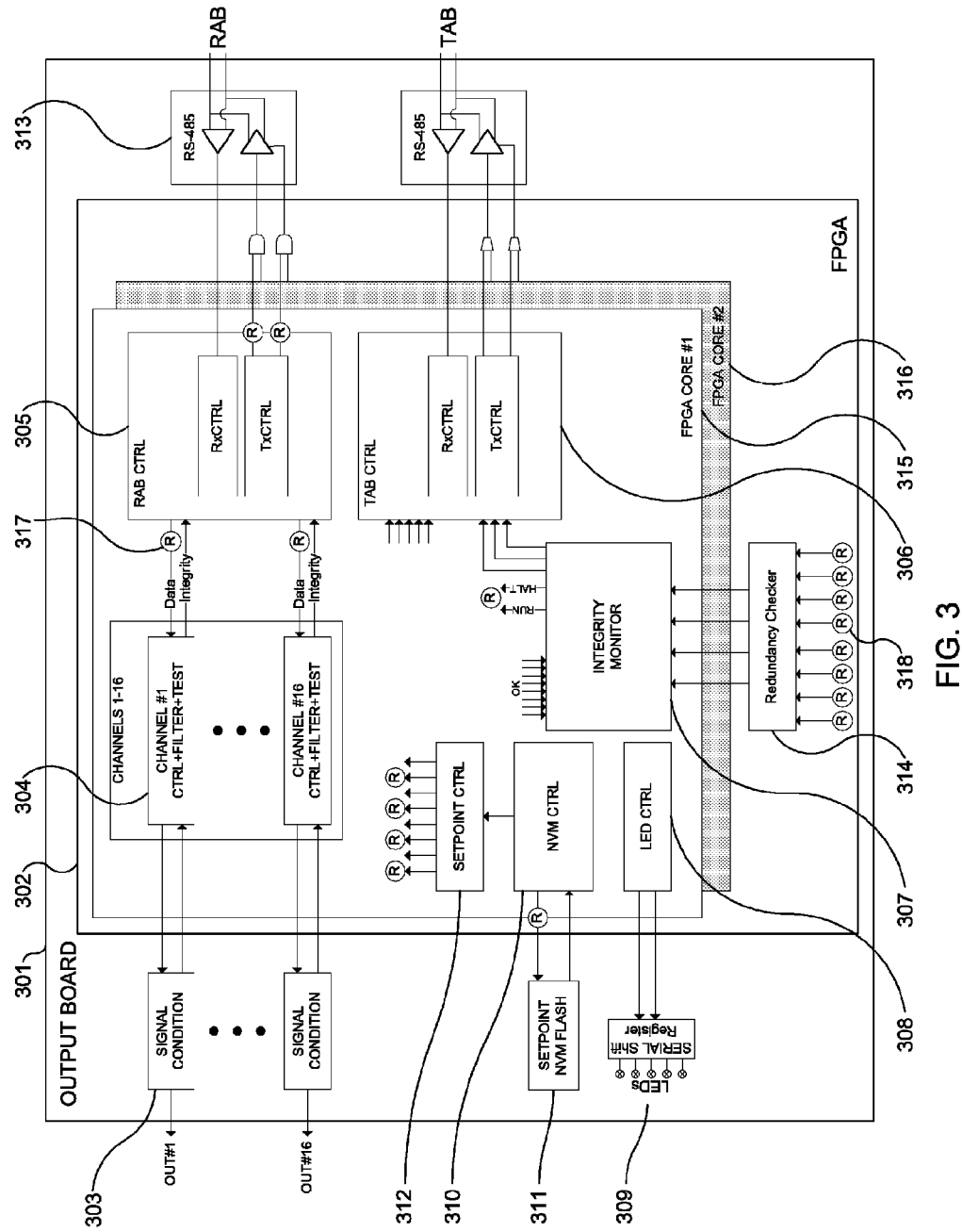
FIG. 3 is a general arrangement of an output control board.

FIG. 3 is a preferred embodiment of a generic output board (OPB) 301. OPBs are commonly capable of driving or controlling a number of outputs. OPBs are typically responsible for controlling or conditioning actuators, indicators, relays, solid state relays, and field output devices. OPBs will typically be dedicated to a specific signal type, such as a 24-48 VDC digital output, a relay output capable of switching a 125 VAC analog signal, a high inductive solenoid load, or a resistive device. The output channel itself can be simple with minimal circuitry to switch a relay, or it can be more complex such as a FET driver channel with feedback measuring and test circuitry to ensure channel integrity. Other output types are controlled current, controlled voltage, controlled resistance, controlled digital communication, and an external communication. Output circuit isolation is preferably at least 1500 volts.

Incorporated into the onboard FPGA 302 is the digital channel portion 304, the Non-Volatile Memory Control 310, Setpoint Control 312, LED Controller 308, Integrity Monitor 307, RAB communication 305, TAB communication 306, and the Redundancy Checker 314.

An output channel preferably comprises a digital circuit 304 and the analog signal conditioning circuit 303. The analog circuit is responsible for signal conditioning from digital control voltage levels (typically 3.3 V) into the desired output function for field output circuits (i.e. switching to an analog voltage, switching a relay or solid-state-contact or a high-power FET transistor). The analog circuit is responsible for all integrity sensing and feedback loops, which provide information about the state of the output circuit. The digital portion of the channel is located in the FPGA 302 and performs all channel control, integrity checks, self-testing and any necessary digital filtering. All digital channel circuits, RAB communications, control, and channel integrity are implemented with redundant logic within the FPGA. The redundancy ensures, in the event of a device failure, the failure is detected and the board is isolated from the rest of the ALS rack. The output board utilizes digital output information from the CLB.

In a preferred embodiment, the OPB has very similar redundancy as the IPB. Various particular key check point circuits 317 are monitored within dual logic cores 315, 316. The check point circuits are then input 318 to the redundancy checker 314 for monitoring and comparison for an exact match.

In a preferred embodiment, self testing functions include any detection of any change in state, detection of any change in data content, and detection of any change in control or integrity circuits. If a problem is uncovered in the self test, the FPGA then causes an associated output circuit to enter a predetermined fail safe mode.

In a preferred embodiment, the OPB has the capability of driving field devices directly from the rack without the use of interposing relays. This is accomplished with the use of well protected FET transistor devices and a specific isolation scheme.

Preferably, output channels are divided into typical groups: one to four groups as is common in the art. Preferably each group uses a common ground and has galvanic isolation from the other groups, as well as the digital portions of the board. Channels and/or groups of channels can typically be configured to perform the intended function (Normally Open/Normally Closed or Fail Safe modes).

The OPB communicates over the RAB 305 and the TAB 306 as requested. The OPB is a slave device on the both the RAB and the TAB, and the communication is preferably via RS-485 (i.e. EIA-485) standard 313. Preferably, OPB's are dedicated to driving or actuating a field output every time a request is made, and the on-board intelligence is limited to the capability of the integrity monitor or redundancy scheme to decide if a failure has been detected. The OPB does not have the capability of broadcasting the failure to the rest of the ALS rack. The core logic board will detect the failure and handle all broadcast responsibilities. The OPB can detect communication failures on the RAB or TAB and is responsible for isolating the board from further communication on the RAB until the failure(s) has been removed.

The OPB has a setpoint configuration by use of a dedicated FLASH device 311 and controller 310 to store application specific setpoints. The Setpoint configuration is stored in an external Non-Volatile Memory (NVM) 311. Typical stored information is similar to information stored in an IPB Non-Volatile Memory. On the OPB, local setpoint copies are maintained and utilized in the FPGA. The amount of Setpoint information stored is commonly between 0-80 bytes.

In a preferred embodiment, the OPB incorporates a Fail-safe feature which allows the OPB to autonomously assume a predefined Failsafe state upon a system failure, such as a loss of communication between boards. The fail safe state for a particular OPB is defined for a particular application. Typically, there are three states for each of the independent channels of a board. The states are: Fail-As-Is, Fail-As-Defined-Open, and Fail-As-Defined-Closed.

The OPB also contains a hardware watchdog in an integrity monitor 307, which times-out after unsuccessful communication after a set period of time, typically greater than 100 ms. This watchdog capability ensures the core logic board will detect a failure and put the OPB into a Failsafe mode.

Preferably, the OPB provides a front panel indication which shows the status of a selected output with an LED in a display 309. The board design will commonly allow for both generic OPB front-panel indications as well as customized front panel indications by mapping a selected LED indication to an application specific field output.

Various problems on the IPB and OPB will not affect communication on the RAB or TAB. For example, when the NVM on a board has a detected failure, the communication on the RAB and TAB are still allowed to continue, and the CLB will take suitable action based on programmed logic.

In a preferred embodiment, the OPB and the IPB are separate to improve reliability and efficiency. However, in another embodiment, a single board contains both input and output channels. In another embodiment, a single board may also contain the process control logic circuits as well as any I/O channels.

The present invention includes the design for a high-integrity Solid-State output board dedicated to drive high-inductive loads at low to medium power levels. Preferably, the output power may be up to 1.5 amps continuously and 5 amps for 100 ms, at a maximum of 175 volts. The Solid-State output board provides a high level of isolation from both field devices and each of the channels on the board. The board is hot swap/pluggable and provides primary-side and secondary-side (field) self-testing capability. The board has a redundant fail-safe power supply sourced from a secondary power source to keep channel states intact after the loss of primary board power. An advanced FET transistor configuration and self-test capability make this board preferred for applications where it is critical to have the capability to (de-)energize when requested.

Figure 4:
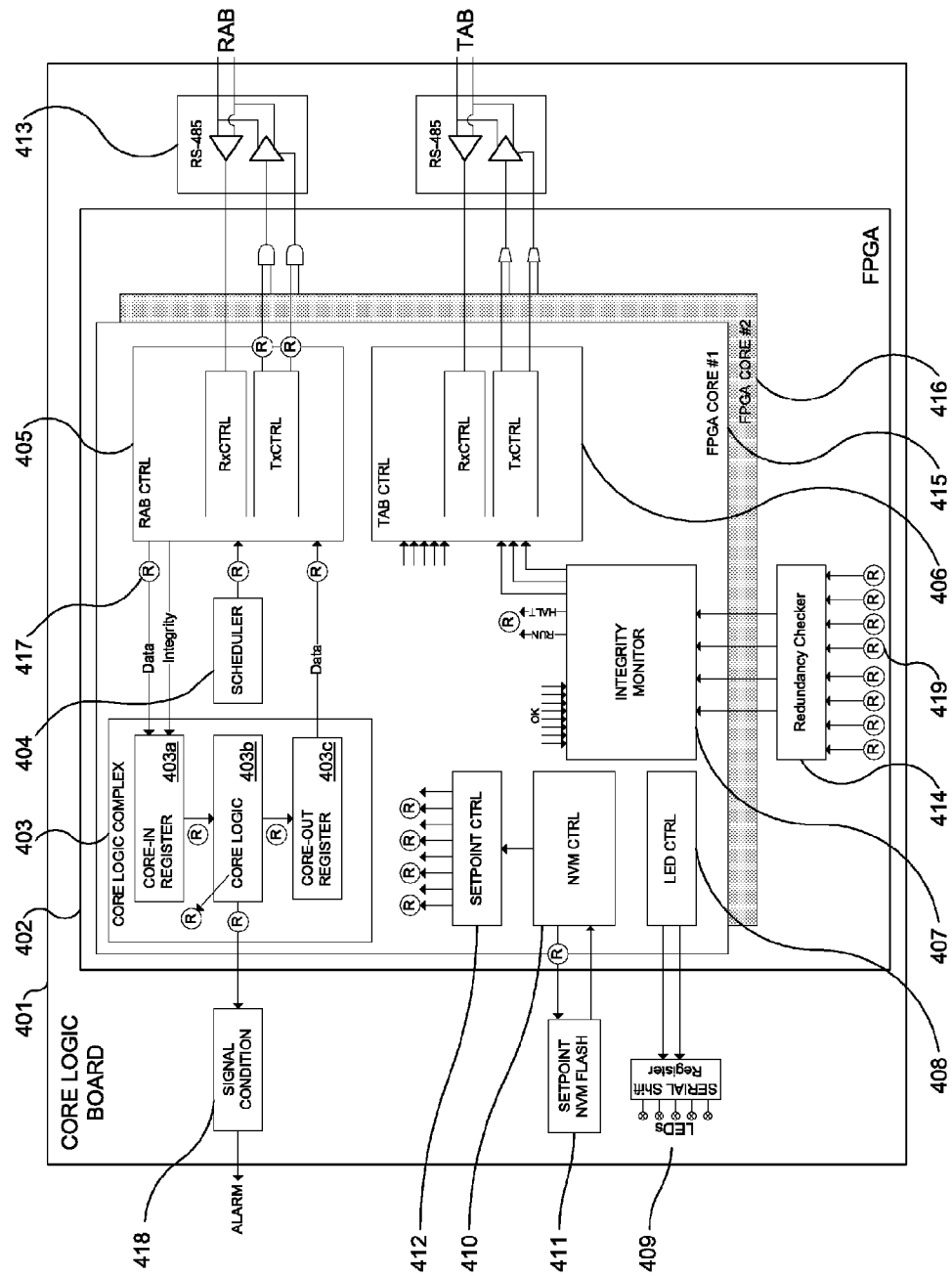
FIG. 4 is a general arrangement of a control logic board.

FIG. 4 is a preferred embodiment block diagram of a generic Core Logic Board 401 (CLB). In this embodiment, the CLB contains all the application specific logic circuits, which define and control the operation of a given process. The core logic circuits are also called the control logic circuits. The CLB controls all sequencing within the ALS system. The CLB issues requests to input boards to provide the digital representation of the field input information as required, makes decisions based on received inputs, and commands the output boards to drive the field devices to a specific output state. The CLB is the primary decision making board in the ALS system. In a preferred embodiment, the system is designed with only one CLB, but systems with 2 or more CLBs are possible if the application should require the extra redundancy. In this case, the CLBs are hot swappable and hot pluggable in the event a CLB needs to be replaced.

The core logic complex 403 consists of three principal sub circuits, the Core-IN register circuit 403a, the core logic circuit 403b, and the Core-OUT register circuit 403c. The core logic circuit 403b receives information and sends communication on the RAB through the Core-IN and Core-OUT registers 403a, 403c. The Core-IN register holds a local copy of the information stored on the IPBs as well as the associated integrity information from IPBs and OPBs. The Core-OUT register holds a local copy of the information which is to be transmitted to the OPBs to control the field outputs.

The core logic 403b is a customizable module which contains the application specific logic circuits. The core logic circuit is implemented based on the requirements of a given application and can contain any type of digital building blocks which can be generated from a NAND2 device, such as AND/NAND/OR/XOR-gates, Flip Flops (D, JK, SR), comparators, counters, timers, sequencers, multiplexers, or Finite State Machines (FSMs). The core logic may include more advanced control functions including: lead control, lag control, PID control, bistable control, and arithmetic circuits to perform a desired mathematical function used for any control function. The size of the core logic circuit can range less than 5K gates (NAND2 equivalents) in simple control systems, to more than 100K gates in more complex systems where advanced arithmetic is required.

The CLB has a dedicated scheduler 404 to control the access scheme for which the CLB access the slave devices such as IPBs and OPBs thru the RAB master bus interface. Preferably, the communication is by an RS-485 standard 413. The preferred access pattern typically includes access to all the input boards and then to all the output boards followed by intentional idle period with out communication. This access pattern is referred to as a 'System Frame'. The scheduler follows a repeating pattern of accessing the input boards, followed by accessing all the output boards and communication boards. Preferably, the cycle time can be set configurable with a value between 1 ms (1000 Hz) and 100 ms (10 Hz). A fully populated ALS system with 62 boards, with one read or write transaction to/from each board, typically has a System Frame rate of 10 milliseconds or less. Slave boards will maintain synchronization to the System Frame by monitoring the communication on the RAB, which is controlled by the CLB.

The scheduler circuit 404 is preferably designed so that it
i) is not modifiable during operation
ii) operates on a fixed predetermined schedule
iii) utilizes a predetermined access time that is not modifiable during operation
iv) provides for uninterrupted access to bus communication
v) provides for protection against any data storm by use the fixed schedule
vi) is implemented in a redundant manner
vii) provides for instant failure detection of the scheduler circuit by use of redundancy The CLB is master on the RAB 405 and initiates all requests on the bus. Communication on the RAB is controlled and synchronized to a System Frame (typically 10 ms). During each System Frame, all boards within the system are accessed. The term access covers a simple bus transaction on the bus interface. The CLB continuously communicates with all ALS boards in a round-robin fashion to collect input data & integrity information from each input board, as well as to write output data to and collect integrity information from all output boards. The CLB continuously monitors all RAB communication and the inherent architecture (protocol and implementation) detects any RAB communication failure.

In the situation where communication fails, such as due to a CRC failure, loss of packet, or similar defect, the scheduler circuit 404 will add the board which failed to respond correctly to a 'Watch List'. A new attempt to communicate with the board will be done in the following system frame cycle. An unsuccessful retry will result in the failing board being added to the 'Removed List' and the system will actuate an alarm to indicate a failure has been detected. Data (or the lack there of) from the failing communication will be isolated (not used) and will not cause any further effects.

The scheduler circuit 404 requests accesses to the slaves over the RAB in a round robin fashion at a fixed predetermined access pattern. The CLB will read information from all appropriate input boards, store the received information in the Core-IN registers 403a, and write information stored in the Core-OUT registers 403c to all appropriate outputs boards. A board can be accessed multiple times if necessary within a System Frame but this is typically not the case.

The CLB is a slave on the TAB 405 and responds to any requests for diagnostic and integrity information. The information can be collected from the CLB in a non-intrusive manner and does not affect the on-going operation of the CLB or the remaining system. Examples of diagnostics information from the CLB are inputs and outputs to the core logic module, any internal node that is of interest to a certain application (such as states in a state machine or the count of a counter), as well as internal health information. The access pattern on the TAB is independent on the scheduler circuit 404 due to the complete independence between the RAB and the TAB.

In a preferred embodiment of the CLB, the circuits within the FPGA 402 are protected with a number of features to ensure the integrity of the circuits. In the ALS platform the RAB 405 and the TAB 406 communications modules, the integrity monitor 407, the LED controller 408, the NVM controller 410, the SetPoint controller 412, the scheduler 404, and the core logic complex 403 are all implemented within each of the redundant logic cores 415, 416 in the FPGA 402. Strategically important signals within or from the different modules are extracted from each of the redundant cores 415, 416 (a typical check point 417 is additionally indicated by the letter R); the signals from a particular circuit from each of the redundant logic cores 415, 416 are wired 419 to a redundancy checker circuit 414. The redundancy checker 414 compares the signals from each of the redundant cores for an exact match. If the values do not match, an FPGA redundancy failure is detected. This will force the CLB into a fail safe state, and all communication on the RAB will be discontinued.

Preferably, the redundant logic is utilized within the FPGA as part of the overall instrument to detect any unintended change of states of any logic within the FPGA device 402. In a preferred embodiment, the redundancy checking circuits provides instant detection of any unintended change, such as:
i) failure of the core logic circuit complex 403
ii) failure of circuitry related to setpoint or the non-volatile memory sub circuits
iii) wrong circuit board inserted into wrong slot ID
iv) power failure provided by any voltage supervisor feedback circuits
v) communication failures including lack of communication and erroneous communication The CLB preferably contains redundant logic circuits that provide for internal error checking. Redundancy comes from internal parallel paths. A block of logic circuits or the entire logic circuit structure processes input digital data to generate a first digital output data. A replicated copy of logic circuits within the CLB then process the same input digital data to generate a second digital output data. The first and second digital output data are then compared within the CLB for equivalency utilizing various gates. If there is a mismatch, an error may then be recognized. This concept may be used to uncover errors within the CLB, or on any other circuit board where redundancy is needed. In a preferred embodiment, a single FPGA includes the replicated logic circuit structure and comparing structure. In another embodiment, pluralities of FPGA's are utilized to provide the redundancy.

Redundancy can be scaled to a suitable level by grouping a desired number of logic circuits. Grouping provides a better understanding of where an error might be coming from, and allows separation of critical and non-critical errors. A preferred embodiment is to utilize two equivalent parallel logic circuits; however, other embodiments would include three or more equivalent parallel logic circuits with an optional voting scheme for appropriate action when logic circuits are not equivalent. Equivalency is based on a chosen criterion at system configuration.

Preferably, an alarm circuit is implemented by the CLB based on a failure condition chosen at system configuration. The alarm is preferable controlled directly from the FPGA and signal conditioned 418 on the board to drive external alarm circuits by use of a electro-mechanical relay or solid state relay driven by the FPGA 402.

The CLB has a dedicated non volatile memory, such as a FLASH device, to store application specific SetPoints used by the design. The SetPoint configuration is stored in the external Non-Volatile Memory (NVM) 411 and local copies are maintained/utilized in the setpoint controller 412 within the PGA. Examples of such configuration SetPoints are: sequencer delays, time constants, process temperature trip value, and trigger-points. Other operating parameters may be stored in the NVM and include channel enable, channel disable, filter timing, normally open/normally closed contact settings, circuit board identification, circuit board serial number, and calibration parameters.

Cyclic redundancy checks are utilized to protect the Setpoint information stored in the NVM. The content of the NVM is read during initial power-up and re-validated at selected intervals for integrity during normal operation. In a preferred embodiment, DIP switches are not used to store setpoints or configuration information. The NVM is also configured to prevent tampering or spurious change during operation.

The ALS has the capability to detect faults while on-line and off-line. The ALS architecture prevents faults from propagating through the system and causing un-intended plant events. In the presence of one or more failures, the ALS system will alarm the condition and isolate the affected portions of the failing board(s) or channel(s). The System Mode of operation is based on the following three modes: Full Capability Operation (FCO), Reduced Capability Operation (RCO), and HALT mode. The CLB is the controlling entity of the System Mode.

FCO: The ALS rack operates in normal mode of operation, and is ready to perform the intended safety function.

RCO: The ALS rack operates in reduced mode of operation, and is still ready to perform the intended safety function. One or more failures have occurred. The system continues to perform as specified and the failing circuitry does not affect the system's ability to perform its safety function. The Core Logic is fully functional. An alarm is generated 418 and maintenance is required.

HALT mode indicates the ALS rack is inoperable and not capable of performing the safety function. The ALS rack enters HALT mode in the situation where any vital-error occurs and the system is "shut down" in a deterministic manner, where all outputs are preserved for system integrity. All operations will stop and the system (i.e. all boards) enters a fail-safe state.

In a preferred embodiment, all logic modules within the CLB FPGA 402 are implemented with redundancy.

In a preferred embodiment, board failure detection is incorporated into any circuit board and the failure detection is preferably done within an onboard FPGA. The CLB receives communication about any on board failure. The CLB will then causes all output circuits to enter an operating mode according to a designed process control criterion or an ALS control criterion previously described. Detected failures may include power failure, channel circuit failure, and failure of the onboard FPGA in any way.

In FIG. 4, The CLB has a dedicated and independent alarm circuit 418 to control and generate an isolated alarm output. Two types of failures can cause the alarm to be actuated: an application related failure or system related failure. An example of an application related failure is where inputs from valve position switches indicates the valve is both open and closed for a time period much longer than the valve stroke time. An example of system related failures are failures on the RAB bus, supply voltages out of specified range or blown fuses, device or circuit failures. Other detectable failures are:

a) input channel circuit or output channel circuit failure b) power failure provided by voltage supervisor feedback circuit c) setpoint or non-volatile memory failures d) wrong circuit board inserted into wrong slot ID e) communication failures including lack of communication and erroneous communication f) redundancy test failure within an onboard FPGA Preferably, a failure within any circuit board is indicated by an alarm or a light, such as an LED 409, on the front of the circuit board. As an alternate or in addition, the fault is detected by the CLB and an important failure activates an alarm circuit or otherwise notifies an operator of a failure.

The integrity of input and output channels are communicated to the CLB through the communication network. Faults may then used to control the modes of any output boards depending upon the type of fault.

Preferably, integrity is maintained within the ALS by utilizing setpoints on each circuit board which stored in an on board non-volatile memory to identify the board, so that the ALS detects an incorrect circuit board that is inserted into a rack. Additionally, slot identification in a rack is provided to match circuit board ID information, so that ALS detects a circuit board that is inserted into an incorrect slot in a rack.

The ALS is also configured to identify a board with an incorrect setpoint parameter stored within the non volatile memory of a circuit board.

Figure 5:
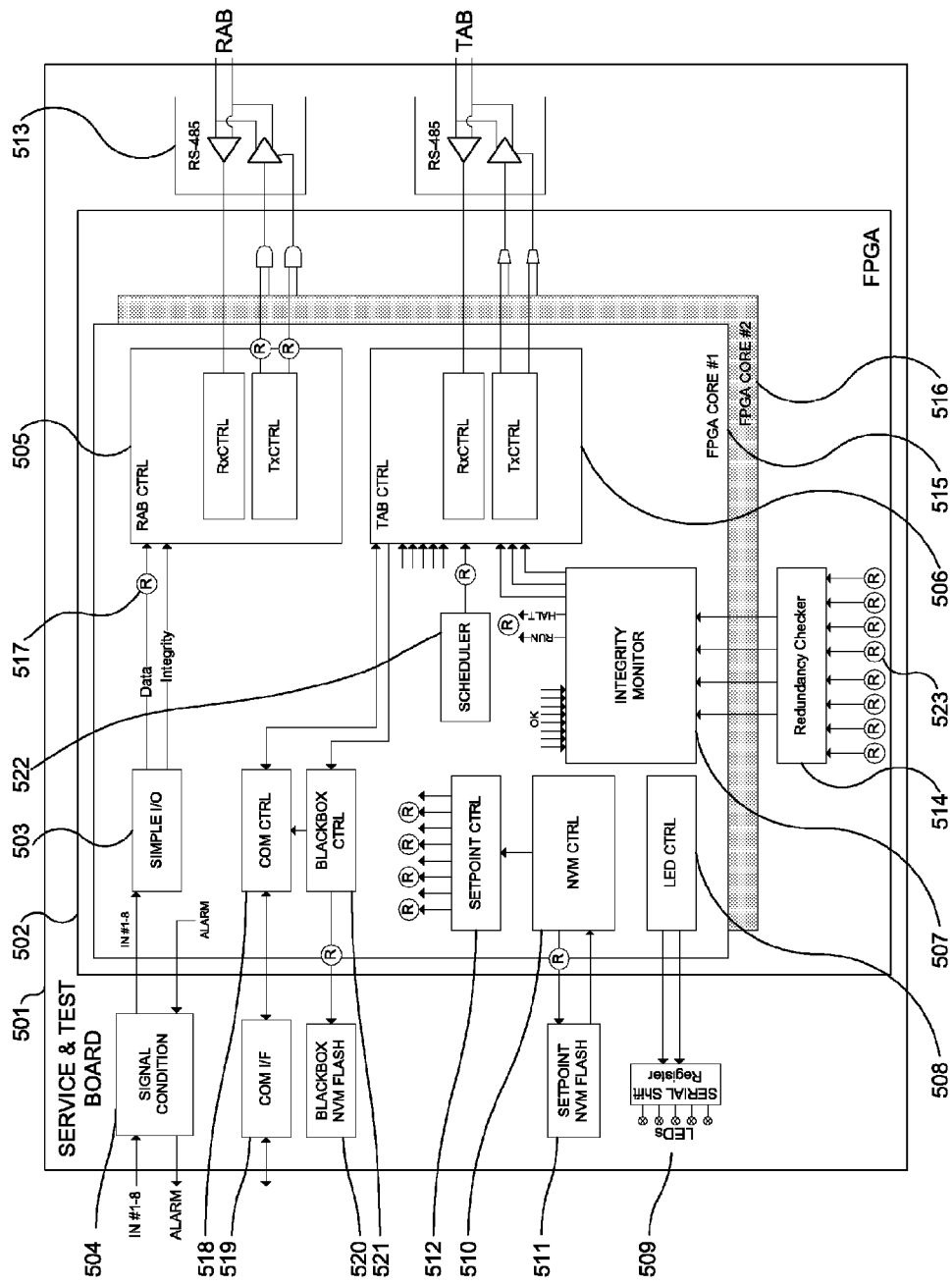
FIG. 5 is a general arrangement of a service and test board.

FIG. 5 is a preferred embodiment of a Service and Test Board (STB) 501. The STB provides several advanced on-line and off-line maintenance features such as integrity monitoring and diagnostics. The monitoring and diagnostic capabilities support installation and post-installation testing, accurate troubleshooting in the event a failure or an unintended plant event occurred during normal operation, maintenance during outages, and maintenance while the system is on-line.

The STB is master on the TAB 506 and initiates all requests on the bus. Communication on the TAB is controlled and synchronized to a System Frame, which typically is delayed to any RAB 505 communication cycles. During each System Frame all boards within the system will be accessed one or more times. Information gathered on the TAB is made available to the BlackBox recorder and diagnostics interface.

The STB is slave on the RAB and responds with the appropriate information when the CLB requests it.

A monitoring module 510 within the STB provides a non-intrusive and independent monitoring of all RAB communication. In the event of un-intended bus operation, the local Alarm circuit will actuate the alarm 511.

In a preferred embodiment, an ALS system contains one and only one STB. However, in another embodiment, the ALS system operates without the STB. Absence of the STB will remove the advanced diagnostics features offered by the board. Multiple STBs in a system are one embodiment of the present invention, and is appropriate in some cases.

Preferably, the STB includes a dedicated FLASH device to store application specific Setpoints used by the design. In a preferred embodiment, the Setpoint configuration is stored in an external Non-Volatile Memory (NVM) 511 and local copies are maintained/utilized in the FPGA 502. Examples of such configuration setpoints are filter constants or front-panel contact types.

Preferably the STB incorporates a run-time diagnostics feature which provides a live-view of all important signals within the ALS through a communication interface such as a USB port 519 which in turn accesses information available on the TAB bus through a communication controller 518. It also preferably incorporates a run-time logging and diagnostics feature. The logging feature is called Black Box or BlackBox. The BlackBox circuit continuously and passively monitors information transmitted on the RAB and retrieves further information on the TAB, and is controlled by the scheduler 522. The information is time stamped by a controller 521 and stored into a separate non volatile memory 520 which allows for post-event analysis. Optionally, a general recording of important system information is stored at a specified interval, or by a predetermined criterion. The recorded information is very useful in diagnosing problems with the process being monitored as well as the ALS. A preferred storage length for data recovery is at least 18 months. In a preferred embodiment, an operator may retrieve information from the Black-Box by a suitable operator interface, such as a USB port.

The service and test board may have outside communication to a remote device through a communication channel which may include various interfaces such as an EIA-422, Profibus (PROFIBUS International), Ethernet (such as IEEE 802.3), USB2, various controlled digital communication outputs, and other external communication outputs. It may also receive various inputs.

In a preferred embodiment, information logged by the BlackBox includes:
 i) input channel date and integrity information
 ii) output channel state and integrity information
 iii) intermediate values within the control logic circuit including finite state machine values and counter values
 iv) system state and system integrity information.

The information to be recorded may be established by a criterion at system configuration. The recorded information can be logged based on data dependent events, such as a changed input value outside of a particular range, or based on time, as in a specified time or time between chosen events. Preferably, the BlackBox is capable of recording information every time a TAB or RAB communication is made. The recording time would normally be in the 100 micro second to 100 millisecond range, and is preferably at least as often as every 10 milliseconds.

The BlackBox controller is preferably implemented by using a FPGA, or alternately, a CPLD, PAL, Gate Array, or ASIC. The BlackBox controller can be incorporated within the FPGA on the service and test board, or preferably, as a separate FPGA with a separate non volatile memory. The use of these types of complex logic devices allows the BlackBox controller to avoid using executable software, but instead implement using simple state machine registers and counter circuits.

In a preferred embodiment, diagnostics information requested by an operator is accessed over the TAB and not the RAB. The diagnostics feature is implemented in a passive and non-intrusive manner and does not affect ALS system performance, or any safety related activities, such as input channel sampling, output channel control, core logic functions, or any RAB bus communication. The hardware implementation prevents any interference from the TAB to the system operation. Diagnostic information would include live process information and ALS information.

Similar to the other I/O circuit boards already described, incorporated into the onboard FPGA 502 is a simple I/O channel 503, the Non-Volatile Memory Controller 510, Set-point Controller 512, LED Controller 508, Integrity Monitor 507, RAB communication 505, TAB communication 506, Scheduler 522, and the Redundancy Checker 514. The FPGA 502 has similar redundancy features with a dual core 515, 516 and redundancy check points 517 which input 523 to a redundancy checker 514 as previously described. A typical RAB or TAB interface may be an RS-485 (i.e. EIA-485) standard 513 and an LED display 509 is utilized. The details of these features do not need to be repeated here as they have already been described. A signal conditioning circuit 504 may be used if required for any input that may be connected to the STB and communicated over the RAB.

In a preferred embodiment, a redundant pair of Power Supply Boards (PSBs) are provided in any ALS rack to provide load sharing and redundancy, which ensures a stable internal rack voltage. Preferably, the power supplies incorporate redundancy and load sharing. However, only one power supply board may be used. PSB's convert a higher supply voltage, such as 100 to 150 volts, to the lower voltage used by the control logic circuits, such as 3 to 6 volts, but may also be 3 to 28 volts in some cases. In the event of a failure, each of the PSB's is capable of supplying the ALS rack with sufficient power to continue un-interrupted operation should the other PSB fail. Preferably, any PSB is hot-swappable and can be replaced while the system is operational. A PSB may contain built in diagnostics to detect an under-voltage and provide an energized normally open contact to indicate the failure. Latch handles with micro switches may be included on the PSB in a manner so that when it is unlocked and removed from a rack, it will automatically power down. Additionally, the same switches can be used to power up the PSB when it is inserted into a rack and then secured into place.

Figure 6:
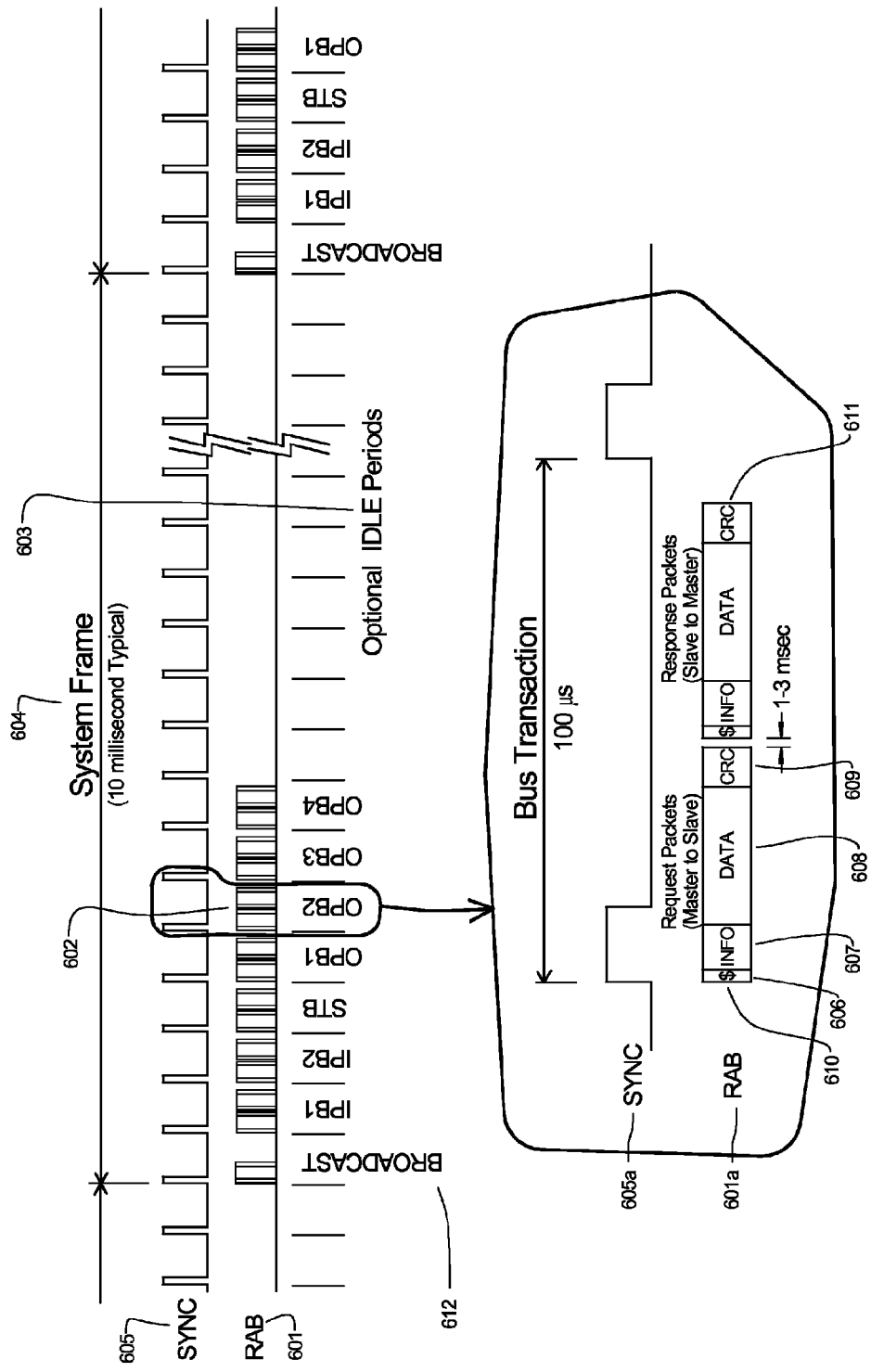
FIG. 6 is a schematic of a communication method on a serial bus.

FIG. 6 shows a preferred embodiment of a typical bus communication method used on the RAB, where the RAB communication use a request-response scheme 601a, where the master (the CLB) sends a request packet 610, and the slave (the IPB, OPB and STB) sends a response packet 611 back in acknowledgement with the requested information. A small time-delay (typically 1-3 ms) separates the request and the response packets to allow for the necessary turnaround from Tx/Rx of the physical layer. All communication on the RAB deploys this request-response scheme, with only one exception being the RAB BROADCAST 612 information packet. This broadcast transaction only contain request packet with information to all slaves, such as a common timestamp for high level board synchronization. Slaves do not respond to a broadcast packet, and the CLB will ignore any response to a broadcast packet.

In another preferred embodiment, the RAB will communicate with the boards in the system in a sequential scheme 601, where the CLB will access typically the input boards IPB1, IPB2, etc and then the output boards OPB1, OPB2 etc. The RAB transactions are typically followed by a number of optional idle periods, 603 i.e. communication slot with no communication. A preferred duration of the idle slots is 0-99 ms. This access scheme encompasses the board accesses and the optional idle periods are referred to as the System Frame 604, and is repeated every 1-100 ms. A preferred embodiment of the System frame is 10 ms (i.e. 100 Hz cycle time) as shown.

The bus transaction includes a request packet 610 and a response packet 611 as shown for a typical OPB2 602. In a preferred embodiment the packets types are similar in structure, but differ in content. In a preferred embodiment of the packet structure 610, the RAB communication uses a common 108 bit packet format. The first 8 bits $ 606 is a simple synchronization-header, the next 20 bits INFO 607 is an information header, the next 64 bits DATA 608 is a data payload, which is then followed by a 16 bit CRC 609 checksum calculated on the 84 bit INFO & DATA fields. The INFO field contains addressing and system information. The DATA payload field contains the digital representation of input data, output data, and integrity information.

The communication method shown in FIG. 6 has inherent safety. The rigidity of the communication schedule hinders other systems from inadvertently communicating on the RAB.

Synchronization between master and slave boards can be achieved in a number of ways. The preferred implementation is implicit synchronization using the inherent communication on the RAB network, where the packet frequency is high enough (compared to crystal temperature drift and ageing), so that synchronization can be done every time a CLB sends a broadcast packet or any other acknowledged packet. An alternative method to ensure synchronization is by the use of an explicit synchronization signal which is broadcasted by the CLB or STB. Synchronization between boards will be in the order of 200 ns or better, but does not need to be better than 1-2us. FIG. 6 is an example where the SYNC 605, 605*a* signal could be internally generated or externally generated.

In a preferred embodiment, the TAB communication is similar to the RAB, but the access scheme differs slightly. The STB is master of the TAB and the CLB is a slave to the TAB. The TAB access scheme is slightly different than the RAB, and the following types of accesses are performed on the TAB:

1. Scheduled BlackBox transmissions. Run-time during normal operation the STB will request and collect board information, integrity and health information and status from all boards within the system. This is done in a scheduled sequence on the TAB, and transmissions occur as point-to-point accesses to each board in the system.
2. Random transmissions. Both run-time and while off-line the STB can initiate a random sequence of reads and writes on the TAB. This type of transmissions are operator initiated, and will only occur if a dedicated piece of test-equipment is attached to the STB and the operator has requested information, such as may be requested to update a display or retrieve system information.

The communication method described for the RAB and TAB ensures a reliable and high integrity communication link. It provides for:
1. Fault Isolation
   a. The bus protocol avoids bus contention, can detect unintended bus contention, and will isolate boards with failing devices.
   b. There is instant detection of communication failure (invalid data) and communication loss (indicating a failing unit).
   c. Spoof proof communication ensures instantaneous detection of any interference from invalid or failing boards. Spoof proof means that a board can not act or appear as another board and spread misinformation.
2. Advanced, Deterministic Protocol
   a. The guaranteed response time allows the system to have a deterministic reaction time for any input state changes.
   b. The guaranteed response time ensures detection of lost or failing devices.
   c. There is guaranteed packet synchronization, with instant detection of any synchronization loss between the master and the slaves.
3. Reliability and High Integrity
   a. Two-way bus communication, which utilizes a request-and-response protocol for transactions, which means all communication, is acknowledged (except Broadcasts).
   b. The packet payload (I/O-data information) is protected by cyclic redundancy check (CRC). Packets are ignored, if the CRC is invalid, and the information not used.
   c. Integrity information collected in the I/O-channels are transferred along with I/O-data. This enables the CLB to make decisions based on valid information and take appropriate action if only invalid channel information is available. If boards become un-available (due to board removal or vital failures) then data and the integrity gets invalidated within the CLB.
   d. Extremely simple synchronization scheme—Local board oscillators are used for local timing references and re-synchronization to the CLB transmissions every 100us.
   e. High noise immunity due to linear bus topology with a reliable standard, such as EIA-485 differential wire-pair, with short wires (typically less than 1 meter and high drive capability. The back-plane provides the main wire-pair with a terminator at each end.

One important innovation of the present invention is an important method used to avoid any stuck-at faults in the safety related data path. The method is to design the circuits in a way that all vital data and control paths are periodically activated so as to uncover hidden faults, such as a low signal path (or transistor output) being stuck-at low due to a device failure, as illustrated in FIGS. 7A and 7B. FIGS. 7C and 7D illustrate the strategy used by the present invention to ensure that the fault will be detected. By overlaying the otherwise static signal with a clock signal, transitions are ensured without changing the resulting state of the signal. Should anything in the circuit described above fail, then there the redundancy checking circuits will detect the failure and deal with the faults appropriately.

In a preferred embodiment every sub-system (such as the input circuits, the output circuits, the logic circuits and the communications circuits) within the system will be tested utilizing the built in self test method just described.

Figure 8:
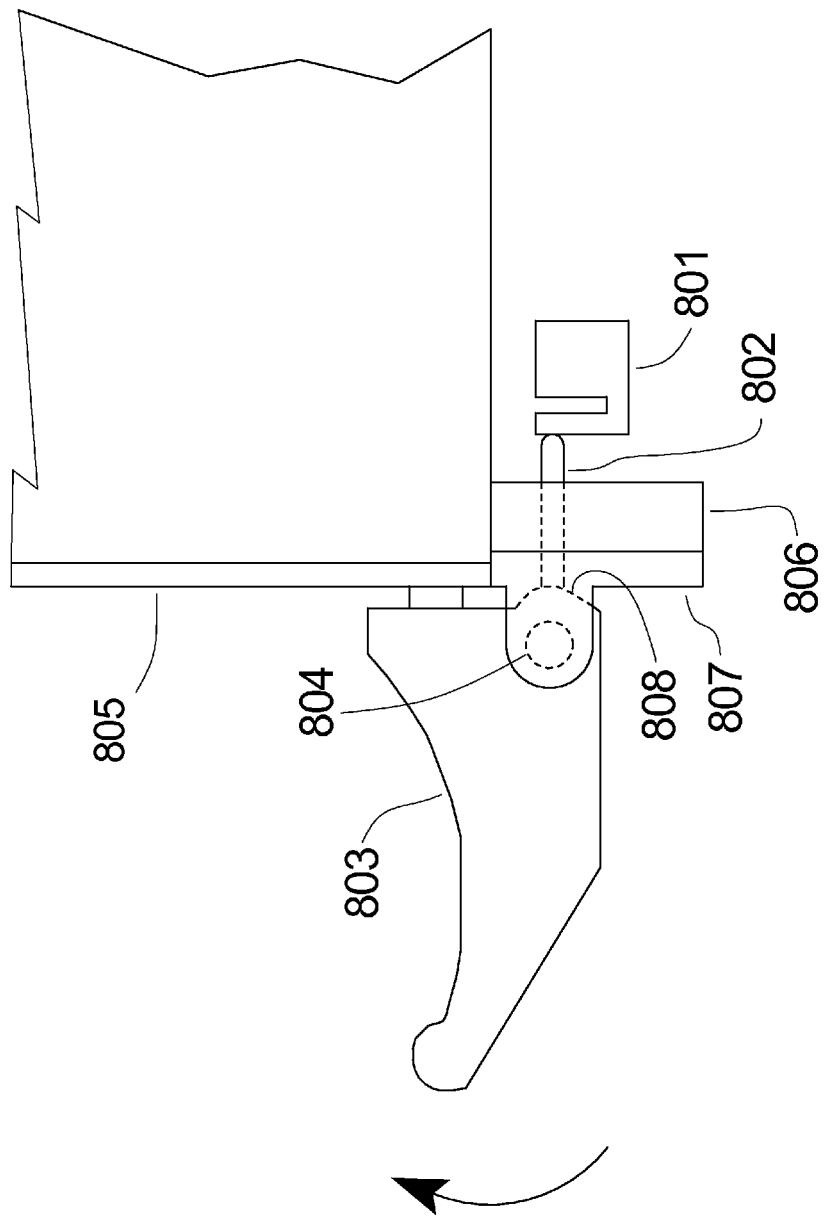
FIG. 8 is an illustration of a latching mechanism for a printed circuit card.

FIG. 8 is an illustration of a method to ensure that a circuit board is monitored for proper insertion into a rack. A lower latch 803 is mounted to the lower front end of a circuit board 805 as illustrated. When the latch end is pushed up, as illustrated by the arrow, the latch pivots around point 804 and a pin 802 pushes into a position activated micro switch 801 by the motion of an eccentric surface 808 on the latch. The micro switch is then activated and the contact closure is detected by a circuit on the board, indicating that the latch is secured. The pivot point 804 is held in place by use of a special holding piece 807 which is attached to the lower rack bar 806. This illustration is only one possible method. Other methods could also be used which could utilize various magnetic or proximity switches.

The latches may also be utilized to power down the board prior to removal and power it up after insertion into the rack. This method provides for safe removal and insertion without creating an electrical arc. It also allows an individual board to be inserted and removed without disturbing the communication on any connected digital serial bus. These features are part of the ability of a board to be hot pluggable (insertion) and hot swappable (removal and replacement by another board) while the ALS operates.

In a preferred embodiment, circuit boards include important self-monitoring capabilities. If any of the following internal tests fail, the FAIL LED is activated on the front of the board and cannot be cleared without a manual reset: unable to synchronize to RAB communication, HALT broadcast from the CLB, illegal access on the RAB bus, a CRC error in the non-volatile memory, a LED read-back failure, an output channel has detected an error (OPB only), missing accesses from ALS, internal redundancy errors detected in the onboard FPGA, 3V voltage supervisor problem, 2.5V voltage supervisor problem, backup power problem for the 5V voltage supervisor, system mode set to halt or reset, attempt to access test functions on the board, both latches open, incorrect BOARD ID, incorrect CHIP ID, and incorrect setpoints.

In a preferred embodiment, on the ALS back-plane there are a number of slots available in the back plane and each slot has a unique ID which is also referred to as the SlotID. The left-most slot in a rack (front view) is location 1 (SlotID #1), the one to the right is SlotID #2, etc. In ALS platforms which require daisy chained ALS racks, the SlotID continues to increment so each slot is unique. The SlotID is allocated on the back-plane for each slot with a 6 bit signal using pull up or down resistors. The ALS board must therefore be inserted only in the slot with a matching SlotID. The SlotID and the BoardID must be the same. In case the BoardID does not match the SlotID, the board will know there is an error and the board will enter a fail safe state (HALT mode) and not allow for any communication on the RAB. The present invention can therefore detect an improper board for a particular slot and will not allow boards to be installed and properly work in an invalid slot. However, other methods of matching board ID's to slot ID's may be used.

In a preferred embodiment, to further protect the system, each board has a unique BoardID related to it's location in the ALS rack or platform. The BoardID will be assigned to the board during configuration and stored in configuration NVM. The ALS rack can accommodate a number of boards per rack, and multiple racks can be daisy-chained together. In a preferred embodiment, the ALS platform can support up to 62 boards in the system. Correspondingly, the RAB and TAB interfaces are designed to address a maximum of 62 units. However, other maximum number of boards could also be used.

In summary, the present invention provides a highly reliable method of monitoring and controlling an safety critical process, such as a plant protection system for a nuclear power plant which requires a 1E system as defined by the Nuclear Regulatory Commission. The present invention is a configured hardware system as opposed to a software based system, with many internal redundant features, which greatly enhances reliability and predictability.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims and all equivalents thereof.

We claim:

1. A service and test circuit board useful for providing integrity and diagnostic monitoring of a hardware based control system comprising:
   a) a redundant core within at least one programmable logic device,
   b) wherein said redundant core communicates to a bus,
   c) wherein said redundant core initiates communication on said bus as a master,
   d) wherein said hardware based control system communicates on said bus as a slave,
   e) wherein said at least one programmable logic device incorporates a redundancy checker and an integrity monitor,
   f) wherein said hardware based control system is configured to provide at least one process function, and
   g) wherein said redundant core incorporates a black box recorder,
   whereby said redundant core provides said integrity and diagnostic monitoring of said hardware based control system by use of said bus.

2. The service and test circuit board of claim 1 wherein said bus is controlled and synchronized to a system frame.

3. The service and test circuit board of claim 1 wherein an external non-volatile memory stores application specific setpoints.

4. The service and test circuit board of claim 1 wherein said black box recorder
   i) continuously monitors information transmitted on said bus, and
   ii) is controlled by a scheduler.

* * * * *